US010601255B2

(12) United States Patent
Pigeon et al.

(10) Patent No.: US 10,601,255 B2
(45) Date of Patent: Mar. 24, 2020

(54) TRANSMISSION OF ENERGY AND DATA USING A COLLIMATED BEAM

(71) Applicant: IBIONICS INC., Gatineau (CA)

(72) Inventors: Michel Pigeon, Ottawa (CA); Steven Prawer, Caulfield (AU); Anne Louise Bruneau, Ottawa (CA)

(73) Assignee: iBionics Inc, Gatineau (CA)

(*) Notice: Subject to any disclaimer, the term of this patent is extended or adjusted under 35 U.S.C. 154(b) by 0 days.

(21) Appl. No.: 16/317,374

(22) PCT Filed: Jul. 20, 2017

(86) PCT No.: PCT/CA2017/050873
§ 371 (c)(1),
(2) Date: Jan. 11, 2019

(87) PCT Pub. No.: WO2018/014131
PCT Pub. Date: Jan. 25, 2018

(65) Prior Publication Data
US 2019/0229558 A1 Jul. 25, 2019

Related U.S. Application Data

(60) Provisional application No. 62/365,144, filed on Jul. 21, 2016.

(51) Int. Cl.
*H02J 50/30* (2016.01)
*H04B 10/114* (2013.01)
*H04B 10/80* (2013.01)
*H02J 50/80* (2016.01)

(52) U.S. Cl.
CPC .......... *H02J 50/30* (2016.02); *H04B 10/1141* (2013.01); *H04B 10/807* (2013.01); *H02J 50/80* (2016.02)

(58) Field of Classification Search
CPC combination set(s) only.
See application file for complete search history.

(56) References Cited

U.S. PATENT DOCUMENTS

| 7,776,024 B2 | 8/2010 | Santini, Jr. et al. |
| 8,368,162 B2 | 2/2013 | Shi et al. |
| 8,649,868 B2 | 2/2014 | Greenberg et al. |
| 2002/0034024 A1* | 3/2002 | Orcutt ............... B81B 3/0062 359/846 |

(Continued)

FOREIGN PATENT DOCUMENTS

CN 103051385 4/2013

OTHER PUBLICATIONS

Diamond encapsulated photovoltaics for transdermal power delivery, Ahnood et al., Biosensors and Bioelectronics 77 (2016) 589-597.

(Continued)

*Primary Examiner* — Omar S Ismail

(57) ABSTRACT

A system, device and method for wirelessly providing power and data to a remote device having a source apparatus generating a modulated collimated beam and a steerable optical element. A remote device with a receiver to convert the modulated collimated beam into an electrical signal which provides a power component for powering the device and a signal component. An uplink channel relays feedback data to position the collimated beam onto the receiver.

17 Claims, 14 Drawing Sheets

(56) References Cited

U.S. PATENT DOCUMENTS

| | | | | |
|---|---|---|---|---|
| 2003/0019931 | A1* | 1/2003 | Tsikos | G02B 26/10 235/454 |
| 2003/0042303 | A1* | 3/2003 | Tsikos | G06K 7/10594 235/384 |
| 2006/0266917 | A1* | 11/2006 | Baldis | H01Q 1/248 250/200 |
| 2007/0019693 | A1* | 1/2007 | Graham | H02J 50/30 372/38.09 |
| 2008/0014897 | A1* | 1/2008 | Cook | H02J 50/40 455/343.1 |
| 2008/0071252 | A1* | 3/2008 | Santini, Jr. | A61F 9/0017 604/891.1 |
| 2009/0248106 | A1* | 10/2009 | Black | A61N 1/3787 607/33 |
| 2011/0144719 | A1* | 6/2011 | Perkins | A61N 1/37217 607/57 |
| 2013/0096661 | A1* | 4/2013 | Greenberg | A61N 1/0543 607/116 |
| 2015/0084438 | A1* | 3/2015 | Beckman | H02J 50/12 307/149 |
| 2015/0304064 | A1* | 10/2015 | Mutalik | H04Q 11/0005 398/48 |
| 2018/0241216 | A1* | 8/2018 | Ishigaki | G05F 1/67 |
| 2018/0243083 | A1* | 8/2018 | Gupta | A61F 2/1624 |

OTHER PUBLICATIONS

Terabit/s-Class Optical PCB Links Incorporating 360-Gb/s Bidirectional 850 nm Parallel Optical Transceivers, Doany et al., Journal of Lightwave Technology, vol. 30, No. 4, Feb. 15, 2012.

Laser Diode Used in 16 Mb/s, 10 mW Optical Transcutaneous Telemetry System, Parmentier et al., 2008 IEEE pp. 377-380 DOI: 10.1109/BIOCAS.2008.4696953.

Design and Optimization of Resonance-Based Efficient Wireless Power Delivery Systems for Biomedical Implants, Anil Kumar RamRakhyani et al., IEEE Transactions on Biomedical Circuits and Systems, vol. 5, No. 1, Feb. 2011.

A Complete 256-Electrode Retinal Prosthesis Chip, Nhan Tran et al., IEEE Journal of Solid-State Circuits, vol. 49, No. 3, Mar. 2014.

* cited by examiner

TRANSMISSION OF ENERGY AND DATA USING A COLLIMATED BEAM

FIELD OF THE INVENTION

The present invention pertains to the transmission of power and data to a remote device using a collimated beam, wherein the device and the source apparatus may move with respect to each other within certain constraints. The present invention also pertains to photovoltaic power and data delivery using a collimated beam to a self-contained device implanted into the body.

BACKGROUND

Size reduction of wireless power and data delivery systems is vital for the development of miniaturised wearable and implanted devices. In the design of implantable technology there is a worldwide drive towards minimally invasive surgical procedures (e.g. laparoscopic surgeries) which necessitates bioimplants with small dimensions. Certain prostheses also have significant geometrical constraints to properly conform to the targeted organs. Delivery of power and data to electronic medical prostheses has been demonstrated in a variety of devices, ranging from the high power consumption devices such as the cochlear implant (Clark, G., 2003, Springer Science & Business Media, New York, p. 459) and retina stimulators (Weiland, J. D. et al., 2005, Annu. Rev. Biomed. Eng. 7 (1), 361-401) to low power prostheses such as spinal cord stimulators (Cameron, T., 2004, J. Neurosurg. Spine 100 (3), 254-267) and cardiac pacemakers (Mallela et al., 2004, Indian Pacing Electrophysiol. J. 4(4), 201-212).

Photovoltaic (PV) cells used in solar panels and other applications convert light into electricity. Sunlight has a broadband spectrum, which yields a low spectral power density that is harvested less efficiently in PV cells. By contrast, a laser emits a collimated beam of light from which it is possible to extract substantially more electrical energy using a PV cell. Matching the photovoltaic cell technology to the wavelength of the incident laser light further improves efficiency. Visible (VIS), near infrared (NIR) and infrared (IR) wavelengths have been used to deliver therapeutic optical treatments in patients. NIR is of particular interest owing to its relatively long tissue penetration depth, and it has been used clinically for non-invasive imaging such as neuroimaging (G. Strangman, D. A. Boas, and J. P. Sutton, Biol. Psychiatry 52, 679 (2002)) and retina photodynamic therapy (U. Schmidt-Erfurth and T. Hasan, Surv. Ophthalmol. 45, 195 (2000)).

Higher power consumption prostheses in the tens of mW require power delivery from external sources. These devices also often require continuous power delivery. Typically these devices are powered wirelessly using inductively coupled coils of significant volume. It is known that the transmitted power of inductively coupled systems reduces rapidly with the reduction in size of the magnetic coil. The geometric constraints of the coils also means that they characteristically occupy large volumes in order to provide sufficient power to the implant and constitute a significant portion of the implant volume, or they are located away from the implant and connected to it with a permanent cable. In the case of a retinal implant, such limitations may require the placement of a permanent cable through the eye wall, thus requiring complex surgery and increasing the risk of complications. This is unlike a photovoltaic (PV) power receiver, where the power density is independent of the receiver volume. A PV receiver can maintain its power density regardless of the dimension. Ahnood et al. (Biosensors and Bioelectronics 77 (2016) 589-597) reported a PV power density in the range of 20 mW/mm$^3$ which compares favourably with the coil based range of 0.01~1.8 mW/mm$^3$, and plays a key role for miniaturization implants. Therefore, PV power delivery is well suited for miniaturised implants.

Diamond capsules are stable in the body, are nontoxic, transparent, and are known for packaging of chronic implants. The wide transmission spectrum of diamond makes it suitable for use as an optical window for PV implants, while the inherent properties of the diamond, such as its mechanical robustness, biocompatibility (Bajaj et al. Biomed. Microdevices 9(6), 787-794, 2007; Tong et al., Mater. Sci. Eng. C43, 135-144, 2014), and chemical inertness (Zhou and Greenbaum, 2010, Implantable Neural Prostheses 2: Techniques and Engineering Approaches. Springer Science & Business Media, New York), make it ideal for use as a long lasting clinical implant. FIG. 1A illustrates a photovoltaic power/data receiver integrated within a diamond encapsulated implant and a diamond optical window tailored to maximise the captured light. FIG. 1B is an image of components of a miniaturised bioimplant as shown in Ahnood et al. (Biosensors and Bioelectronics 77 (2016) 589-597).

Diamond electrodes comprising a plurality of electrically conductive elements made from a nitrogen doped diamond material can also be electrically integrated in the bioimplant, as described in US2014/0094885. Thus, such a capsule and electrodes form an integrated diamond package eliminating any potential break in the seal at each electrode. In the absence of external wiring, the only seal in the capsule is the welding of the top and bottom halves of the capsule. The laser welding of a gold active brazing alloy (Au-ABA) for joining two diamond capsule halves to create a biocompatible, hermetically sealed joint has been demonstrated in Lichter et al. (Biomaterials 53, 464 (2015)). The biostability of gold active brazing alloy (Au-ABA) has been further assessed with the implantation of Au-ABA into the back muscle of pigs (Ahnood et al., Biosensors and Bioelectronics 77 (2016) 589-597), showing no corrosion after 12 weeks. The delivery of power and data to a self-contained implant without any external wiring calls for the encapsulation of the device microelectronics and of the PV cell in an optically transparent capsule, whose properties include hermeticity, biocompatibility and long term stability. Ahnood et al. (Biosensors and Bioelectronics 77 (2016) 589-597) have demonstrated the safe, compact and robust use of transdermal power delivery through photovoltaic cell technology. The PV cell delivered 20 mW/mm$^3$ transdermally, whilst the diamond capsule remained stable in the tissue with no degradation over a period of 6 months in a guinea pig animal model. Although bare diamond reflects a significant portion of light, methods such as anti-reflective coating, surface texturing, and nanostructures can be used to virtually eliminate reflective losses, particularly for a targeted wavelength.

There remains a need for a system and method for transmission of power and data to a remote device from a collimated beam, wherein the device and the source apparatus may move with respect to each other within certain constraints.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a system for wirelessly providing power and data to a remote device using a collimated beam. Another object is to provide a photovoltaic power and data delivery system using a collimated beam to a self-contained device implanted into the body.

In an aspect there is provided a system for wirelessly delivering power and data to a remote device, the system comprising a source apparatus comprising: a light source for generating a modulated collimated beam; a steerable optical element; and a wireless uplink receiver; and a remote device comprising: a receiver for receiving modulated light from the modulated collimated beam and converting the modulated light into an electrical power component and a signal component; a processing unit for processing the signal component; a power conditioning unit for processing electrical energy from the power component for powering the device; an illumination detector for determining an illumination of the optical signal reaching the PV cell; and an uplink channel in communication with the wireless uplink receiver to relay feedback data related to collimated beam alignment to position the steerable optical element.

In an embodiment, the source apparatus and the wireless device are positionally independent and free to move with respect to one another. In another embodiment, the uplink channel relays uninterrupted feedback data.

In another embodiment, the receiver comprises a PV cell for receiving the electrical power component and a photodiode for receiving the signal component. In another embodiment, the received comprises a PV cell and a splitter for splitting the output from the PV cell into an electrical power component and a signal component.

In another embodiment, the remote device is a microelectronic device. In another embodiment, the steerable optical element comprises a reflecting optical element. In another embodiment, the reflecting optical element comprises a Micro-Electro-Mechanical Systems (MEMS) mirror, a curved mirror, or a combination thereof.

In another embodiment, the steerable optical element includes a transmitting optical element. In another embodiment, the optical element comprises one or more exterior lens, intraocular lens, surgical cornea shaping, fibre optic transmission and contact lens, the combined purpose of which is to direct the beam onto the device In another of the collimated beam is a light emitting diode. In another embodiment, the optical transmitter is a laser, or a near infrared laser. In another embodiment, the collimated beam has a wavelength of between 600 to 1540 nm. In another embodiment, the modulated optical signal is received at the remote device at a sufficient rate to support real-time transfer of information. In another embodiment, the source apparatus further comprises a camera. In another embodiment, the processing unit in the remote device is a microcontroller.

In another embodiment, the remote device is a bioimplant. In another embodiment, the bioimplant further comprises at least two electrodes for delivering an electrical pulse to tissue based on received data, for sensing a tissue electric field around the electrode, or both.

In another embodiment, the remote device comprises an electrode array. In another embodiment, the system comprises a plurality of remote devices. In another embodiment, the source apparatus comprises a plurality of collimated beams.

In another embodiment, the remote device is a retinal implant, visual cortex stimulator, mid-brain implant, spinal cord stimulator, cochlear implant, neuronal recorder, neuronal stimulator, cardiac pacemaker, cardioverter defibrillator, recording device, neuromuscular stimulator or drug pump. In another embodiment, the uplink channel transmits telemetry, locational motion data, intensity data, or a combination thereof. In an embodiment, the uplink channel consists of radiofrequency, light emitting diode, or optical reflection modulation transmission In another aspect there is provided a wireless device for receiving power and data from a modulated collimated beam, the device comprising: a receiver for receiving modulated light from the modulated collimated beam and converting the modulated light into an electrical power component and a signal component; a processing unit for processing the recovered signal; a power conditioning unit for processing electrical energy from the power component for powering the device; an illumination detector for determining an illumination of the optical signal reaching the receiver; and an uplink channel to relay feedback data related to collimated beam alignment for positioning the modulated collimated beam on the receiver.

In another embodiment, the receiver comprises a PV cell for converting an optical signal from the modulated collimated beam into an electrical signal and a splitter for splitting the electrical signal from the PV cell into a power component and a signal component. In another embodiment, the receiver comprises a PV cell for receiving the electrical power component and a photodiode for receiving the signal component.

In an embodiment, the processing unit in the remote device is a microcontroller. In another embodiment, the device is a bioimplant. In another embodiment, the bioimplant comprises at least one electrode for delivering at least one electrical pulse to tissue based on received data, for sensing a tissue electric field around the electrode, or both.

In one embodiment the receiving unit comprises a PV cell and a photodiode.

In another embodiment, the device is a wearable device. In another embodiment, the remote device comprises an electrode array. In another embodiment, the remote device is a retinal implant, visual cortex stimulator, spinal cord stimulator, cochlear implant, neuronal recorder, neuronal stimulator, cardiac pacemaker, cardioverter defibrillator, recording device, neuromuscular stimulator or drug pump.

In another embodiment, the uplink channel transmits information about motion, received intensity, or a combination thereof. In another embodiment, the remote device is in a transparent capsule. In another embodiment, the transparent capsule is a diamond capsule. In another embodiment, the source apparatus is connected to the Internet, optionally via a modulated collimated beam. In another embodiment, the collimated beam of the source apparatus is pulsed at a high power for a short duration after remote device tracking acquisition and is returned to an average modulated signal power for the balance of the period.

In another aspect there is provided a method for fine tracking a location of a wireless device by a collimated beam, the method comprising: directing the collimated beam onto a receiver divided in a plurality of segments; measuring an illumination received by each of the plurality of segments; reverse linking each of the plurality of segments to feedback values related to measured beam intensity; and aligning the collimated beam onto the receiver based on the feedback values using steerable optical elements. In an embodiment, the plurality of segments is three or more. In another embodiment, the receiver comprises at least one PV cell. In another embodiment, the collimated beam is a laser beam. In another embodiment, the collimated beam is a light emitting diode.

BRIEF DESCRIPTION OF THE FIGURES

For a better understanding of the present invention, as well as other aspects and further features thereof, reference is made to the following description which is to be used in conjunction with the accompanying drawings, where:

in FIG. 4A the beam appears to originate directly in front of the eye for a wide range of eye positions; in FIG. 4B the collimated beam is steered using eye optics, cornea shaping or a contact lens; in FIG. 4C, the collimated beam is steered by an arrangement of fibre optics; and FIG. 4D illustrates the switching of an array of collimated beams;

FIG. 9B illustrates a correct estimation of the center of the PV cell using this system while

DETAILED DESCRIPTION OF THE EMBODIMENTS

Figure 1A:
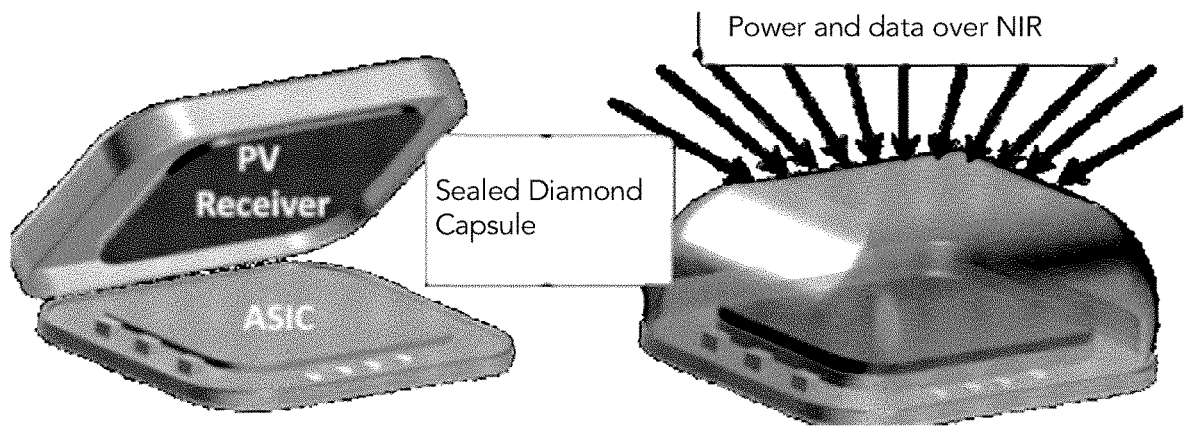
FIG. 1A illustrates a photovoltaic power/data receiver integrated within a diamond encapsulated implant and a diamond optical window tailored to maximise the captured light.
Figure 1B:
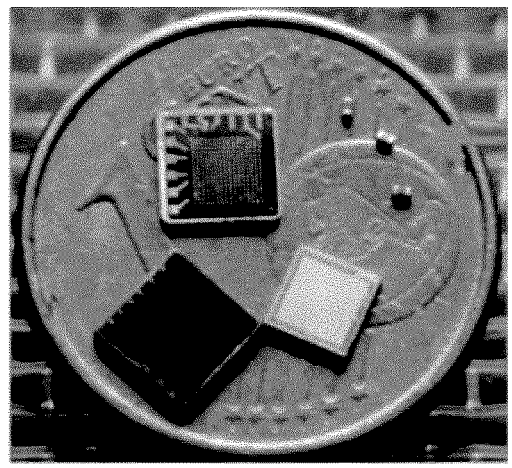
FIG. 1B is an image of components of a miniaturised bioimplant.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or element(s) as appropriate.

The term "signal", as used herein, refers to an electric current or electromagnetic field or light used to transfer data from one place to another and includes but is not limited to one or more electrical signal or electromagnetic wave, analog or digital signal, data, one or more computer or processor instructions, messages, a bit or bit stream, or other means through which data can be received, transmitted and/or detected. The term "light" is defined herein as comprising electromagnetic waves that are within or near the visible spectrum and includes ultraviolet, infrared and near infrared radiation.

The term "software", as used herein, includes but is not limited to, one or more computer or processor instructions that can be read, interpreted, compiled, and/or executed and that cause a computer, processor, or other electronic device to perform functions, actions and/or behave in a desired manner. The instructions may be embodied in various forms like routines, algorithms, modules, methods, threads, and/or programs including separate applications or code from dynamically linked libraries.

The term "transparent" as used herein refers to the property of a material through which light can travel macroscopic distances without significant attenuation. Optical loss can result from absorption, reflection or refraction or scattering of light by a material. In the presently described device, when a PV cell is housed inside a transparent capsule, the capsule must be reasonably penetrable by collimated light at the required wavelength in order to transfer power and data through the capsule material to the PV cell.

The term "capsule" as used herein describes a case, housing or container which encapsulates the electronics of the device comprising the PV cell. In some embodiments, the capsule is biocompatible, durable and hermetically sealed to protect the interior electronics from the surrounding biological environment. The capsule is preferably impermeable to air, gas, and fluid to provide long term stability and/or biocompatibility.

The terms "implant" and "bioimplant" as used herein refer to a microelectronic device that is implanted into a human or an animal. This includes but is not limited to prostheses, sensors and treatment delivery systems. The term "bionic" as used herein means implantable.

As used herein, the terms "uninterrupted" or "continuous" power and data transmission refers to the fact that the power harvested at the remote device is sufficient to power electronic components such as an ASIC, a receiver, a transmitter, stimulating and sensing electrodes and moving parts on a continuous basis, as long as the function of the device is relevant. For example, since the normal eye has no vision during a blink, interruption of power and data during a blink would have no relevance, and would not affect the continuous nature of the transmission as the remote device recovers quickly.

As used herein, the phrase "the source apparatus may move with respect to each other within certain constraints" means that the source of power and the receiver are able to move with respect to each other while still being able to communicate. In particular, the remote device and source apparatus may move with respect to each other but be spatially separated from one another and not tied or attached together mechanically.

Herein is provided a collimated beam-based system to wirelessly provide power and data to one or more remote devices wherein the device and the source apparatus may move with respect to each other within certain constraints. The power and data may also be continuous. Additionally, the system is capable of delivering photovoltaic energy and data to a miniaturised implant in the body which is self-contained and is maintenance-free. The system supports forward and reverse wireless data links. The power harvested from the system is sufficient to power electronic components such as an ASIC, a receiver, a transmitter, stimulating and sensing electrodes and moving parts. The recovery circuitry associated with PV cell is small and can provide data and power to small scale devices. Thus, the present device and system eliminates the need for external wires, batteries and servicing, which is highly desirable for embedded devices residing in an environment not easily accessible, such as inside the body. In one embodiment, the source of the collimated light is an LED. In a preferable embodiment, the source of the collimated light is a laser.

Miniaturising microelectronic prostheses, biocompatible inert encapsulation and photovoltaic cell technology supported by locking of the collimated beam alignment onto the remote device allows placement of the device using minimally invasive surgical procedures, with a number of important medical benefits. Furthermore, it widens the application scope, allowing the photovoltaic device to more readily to conform to geometrical restrictions of various body organs without the risk of tissue damage. Photovoltaic energy and data delivery with a combined optical power and data link can be used in various bioimplant applications such as retinal, brain and subdermal implants, deep brain stimulators, pacemakers and drug pumps.

The present collimated beam-based system may also be used to provide remote power and data in environments incompatible with metallic circuitry, such as a device inside strong magnetic field like a magnetic resonance imaging chamber, or MRI. The present collimated beam-based system can also be used to power and provide data to implantable medical microdevices. For a bionic application, the device, including the photovoltaic cell, must be completely encapsulated in a transparent, hermetic and biocompatible capsule. In a preferable embodiment the optically transparent capsule is a diamond capsule. By selecting the wavelength, the collimated beam can traverse living tissues, including the skin. Matching the collimated beam wavelength to the maximum photovoltaic cell efficiency maximizes the energy harvested by the PV cell to power a remote device. This is important since safety standards limit the intensity of the collimated beam that can be sent toward the body and to the device. Data from a study by P. T. Theilmann (Wireless Power Transfer for Scaled Electronic Biomedical Implants, Thesis submitted to University of California, San Diego, 2012) provides an indicative illustration of dependence of the maximum achievable power density in the body, within the relevant safe exposure limit, to the volume of the power receiver. Power delivery density of PV receivers remains constant with volume, whereas that of wireless coils drops rapidly with volume at small dimensions.

The present system consists of a collimated beam focused on a miniaturised PV cell. In order to provide uninterrupted power and data to a device wherein the device and the source apparatus may move with respect to each other within certain constraints, there is a need for a tracking mechanism which keeps the collimated beam pointed at the device. The tracking mechanism locks the collimated beam onto the device in the presence of relative movement of the device, such as the eye movements for a retinal implant.

Figure 2A:
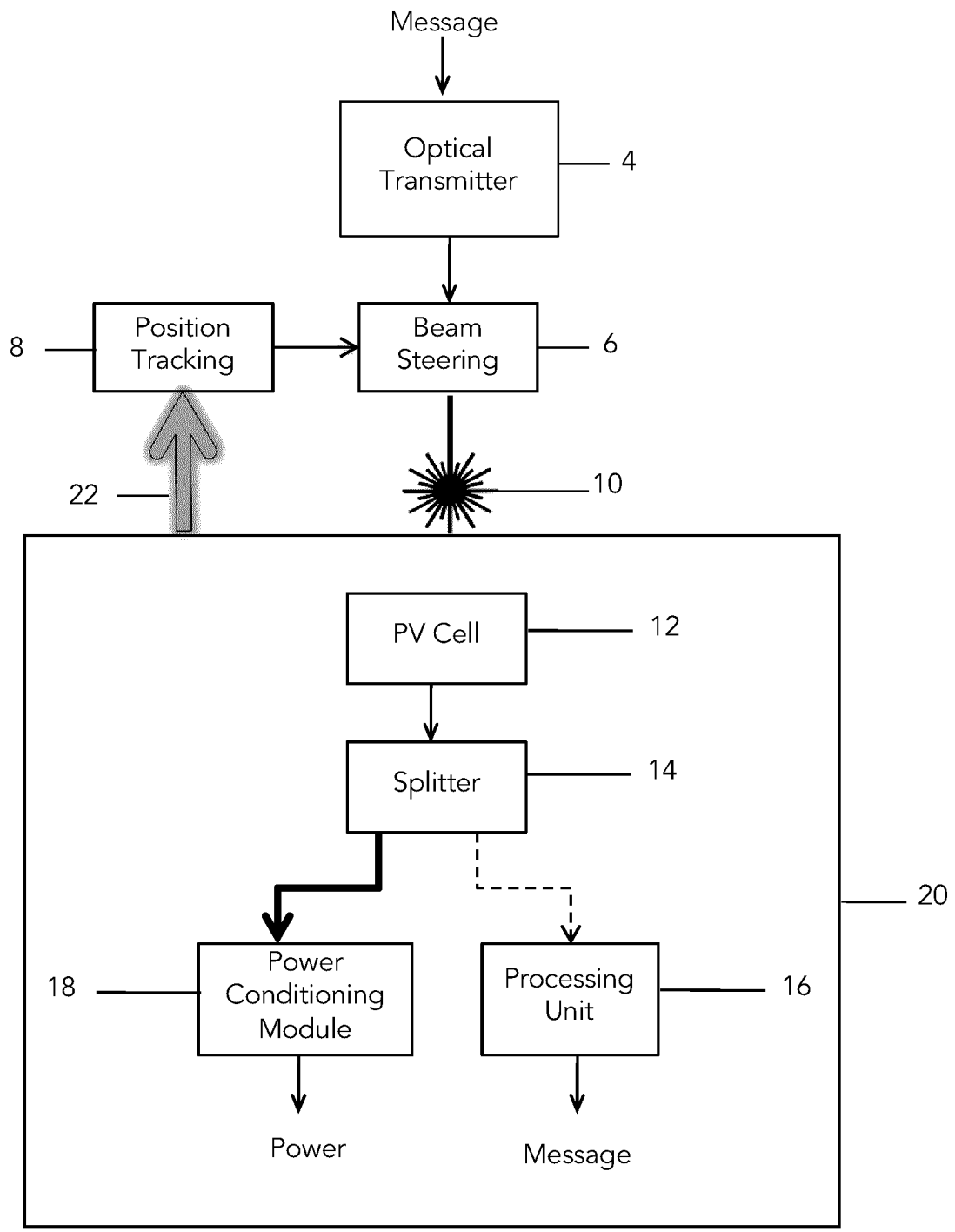
FIG. 2A illustrates a system for remotely supplying power and data to a remote device via a wireless optical link using a collimated beam in which collimated light impinges upon a PV cell from which power and data is extracted.
Figure 2B:
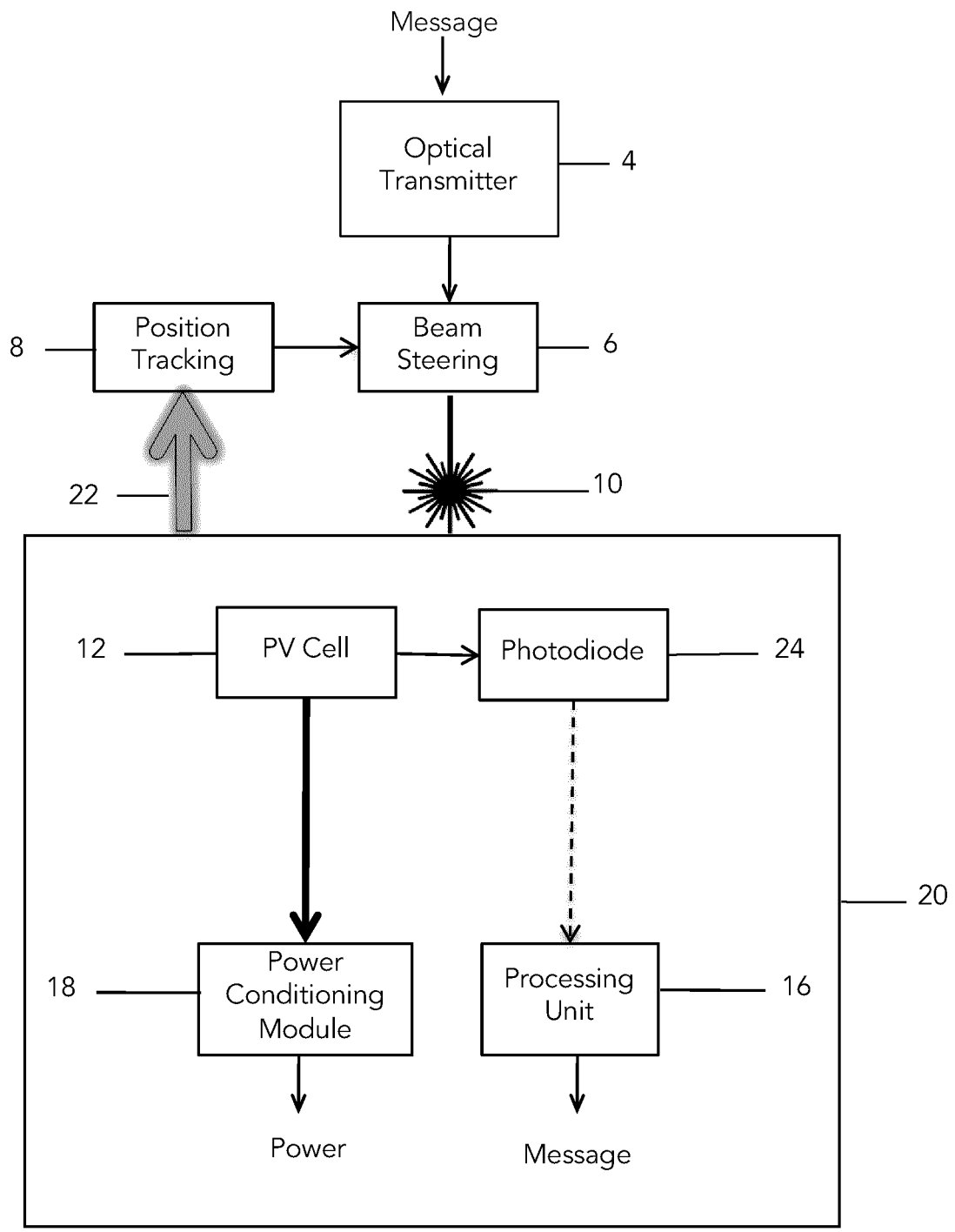
FIG. 2B illustrates a system for remotely supplying continuous power and data to a remote device via a wireless optical link using a collimated beam in which collimated light impinges upon a PV cell from which power is extracted and a separate photodiode from which data is extracted.

FIGS. 2A and 2B are two embodiments of the presently remote device. FIG. 2A illustrates a system for remotely supplying power and data to a remote device via a wireless link using a collimated beam 10 with a PV cell 12 and splitter 14. A message is encoded and relayed to an optical transmitter 4. A photovoltaic cell 12 inside the remote device 20 converts the collimated beam 10 to an electrical signal. This signal is fed to a splitter 14 which delivers signal to a processing unit 16 for extraction of a signal sent by the collimated beam 10. The bulk of the signal power is diverted to a power conditioning module 18 that harvests the energy from the signal for powering the device. A reverse signal 22 from the device is picked up by the position tracking 8, which then provides steering correction to the beam steering 6 in order to keep the collimated beam 10 positioned onto the device. The source apparatus has access to a source of power which is sufficient to operate its components. The source of power can be, for example a battery. FIG. 2B illustrates a system for remotely supplying continuous power and data to a remote device via a wireless optical link using a collimated beam in which collimated light impinges upon a PV cell 12 from which power is extracted and a separate photodiode 24 from which data is extracted. In this case, the light from collimated beam 10 is received by both the PV cell and the photodiode 24. The output from the PV cell provides power to the device via the power conditioning module, and the photodiode 24 provides the data stream to the device via the processing unit. The PV cell may also provide power to the photodiode 24 to reverse bias the photodiode 24. In this way, the embodiment shown in FIG. 2B can have a receiver which comprises both PV cell and photodiode working together such that the incoming collimated light signal is received by both PV cell and photodiode. The PV cell and the photodiode can be independent and wired together, or could also be on the same chip. This increases the flexibility of the receiver to accommodate faster data bandwidths.

Data Transmission

Communications or signal that flows from a source apparatus to the device is called forward data, downlink data or the downlink, whereas communications or signal that flows from the device side to the external apparatus is called reverse data, uplink data, uplink channel or the uplink. Wireless technologies such as radiofrequency (RF) and optical links support very high data rates. In a miniaturised stand-alone system, it is the limited power budget and space to fit microelectronic circuits that limit the achievable data rates. Tran et al. (IEEE Journal of Solid-State Circuits, Vol. 49, No. 3, March 2014) describe a retinal prosthesis chip with inductive links with a forward bit rate of 600 kbps and a reverse bit rate of 100 kbps on a 256-electrode retinal implant using magnetic coils as the means of signal transmission and power. In this system, each downlink data bit is repeated 5 or 10 times for robustness, yielding an actual forward bit rate on reception of 120 kbps or 60 kbps, respectively. A data rate of 16 Mbps has also been demonstrated in a laser diode transcutaneous telemetry system through a skin thickness of 4 mm with a consumption of 10 mW or less using a laser diode (Parmentier et al. Biomedical Circuits and Systems Conference, November 2008. BioCAS 2008. IEEE pp. 377-380). Bidirectional point-to-point communication at these rates makes it possible to support the exchange of different types of messages between the source side and the device side.

Data transmitted between the source apparatus and remote device can be used to perform various tasks in the remote device based on the rates of data transfer. Some non-limiting examples of such communications include configuring parameters in the remote device; sending real-time data to the device for output to an electrode array; and/or receiving telemetry or real-time data from a sensing device that takes measurements in its environment. In one example, a retinal implant receives the data corresponding to a visual scene captured by an external camera and uses it to apply electrical impulses to the retina. In one embodiment, an external camera captures video, or multiple images a second, which is transmitted continuously to the device. Another example of use of the remote device is a sensor implant which reports on the electrical activity in its surroundings or the measurement of a substance in the blood.

Figure 3:
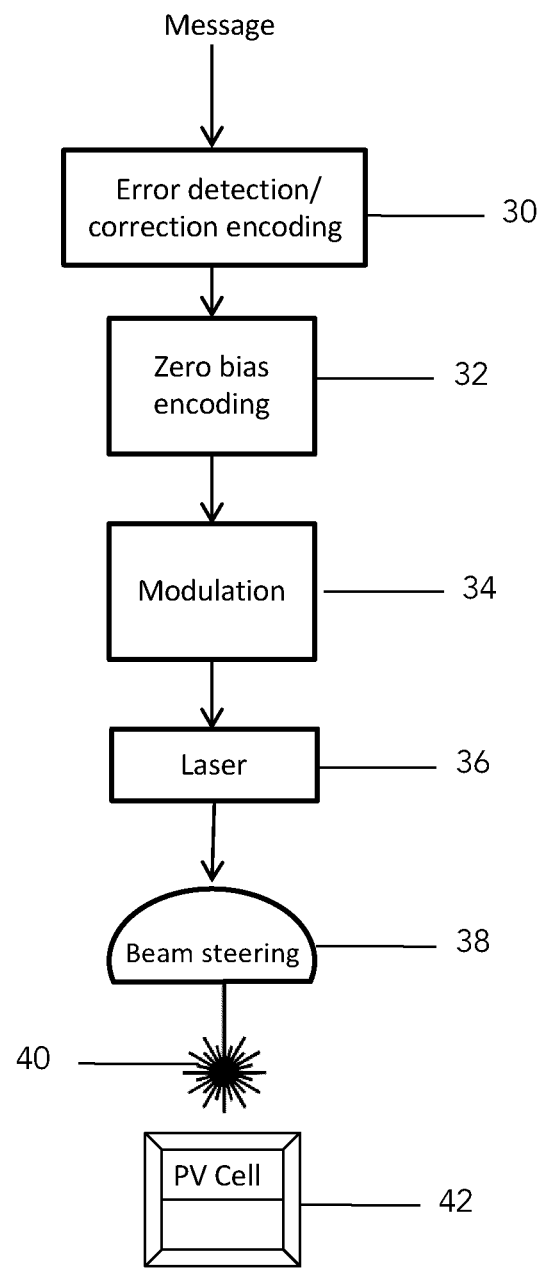
FIG. 3 is a block diagram of data processing and modulation of the collimated beam.

FIG. 3 is a block diagram of data processing and modulation of the collimated beam on the source apparatus. To detect and attempt to correct errors that may be introduced in the transmission channel, error detection and correction methods 30 may be utilized, such as repetition codes, parity bits, checksums, cyclic redundancy checks (CRC), or error-correcting code. Methods are selected on the basis of the type of errors expected in the system, required robustness of the correction method, and ease of implementation. Zero-bias encoding 32 can also eliminate the DC component or bias of the data signal, which occurs when there are an unequal number of bits having a value of zero and one. Additionally, the selected encoding method can make the data self-clocking, so that the clock can be recovered directly from the data signal at the receiver. A zero-bias encoding self-clocking line code such as Manchester is preferable to be applied to the baseband data. Modulation 34 is the process of converting an input into a signal that has the desired characteristics for the collimated light source 36, the channel and the application. Modulation 34 may be unnecessary, and as such it is optional. Several modulation schemes can be considered, including amplitude modulation, frequency modulation, pulse amplitude modulation, as well as orthogonal and multi-level symbol encoding schemes.

The collimated light source 36 is selected to match the PV cell in the remote device in terms of wavelength, and be sufficiently powerful to allow the harvested energy to operate the device. One illumination source during transdermal power delivery experiments using diamond encapsulated photovoltaics was a 980 nm 330 mW Fibre Bragg grating wavelength-stabilised laser (Thorlabs PL980P330J) (Ahnood et al., Biosensors and Bioelectronics 77 (2016) 589-597). The beam steering 38 then directs the collimated beam 40 onto the PV cell 42 in the remote device.

Beam Steering

The position tracking and the beam steering form the tracking system, which steers the collimated beam so that it falls onto the device at all times. A change in device position is detected by the position tracking which sends a corrective signal to the beam steering. The beam steering must be capable of configuring the new setting rapidly enough to ensure illumination of the device by the collimated beam. There are several types of movement associated to the eye. Saccades, the fastest of these movements, last from 30 msec to more than 100 msec with an angular speed of up to 700°/sec for movements of 40° or less (Agarwal, A. et al., Manual of Neuro-Ophthalmology, $2^{nd}$ Edition, Jaypee Brothers Medical Publishers Inc., 2015). Saccade angular speed is a function of the saccade amplitude in degrees. Experimental data collected by D. Schmidt (Aviat. Space Environ Med. 1979 April; 50(4):393-5) shows that for amplitudes less than to 15 degrees, most saccades fall under 400°/sec.

Figure 4A:
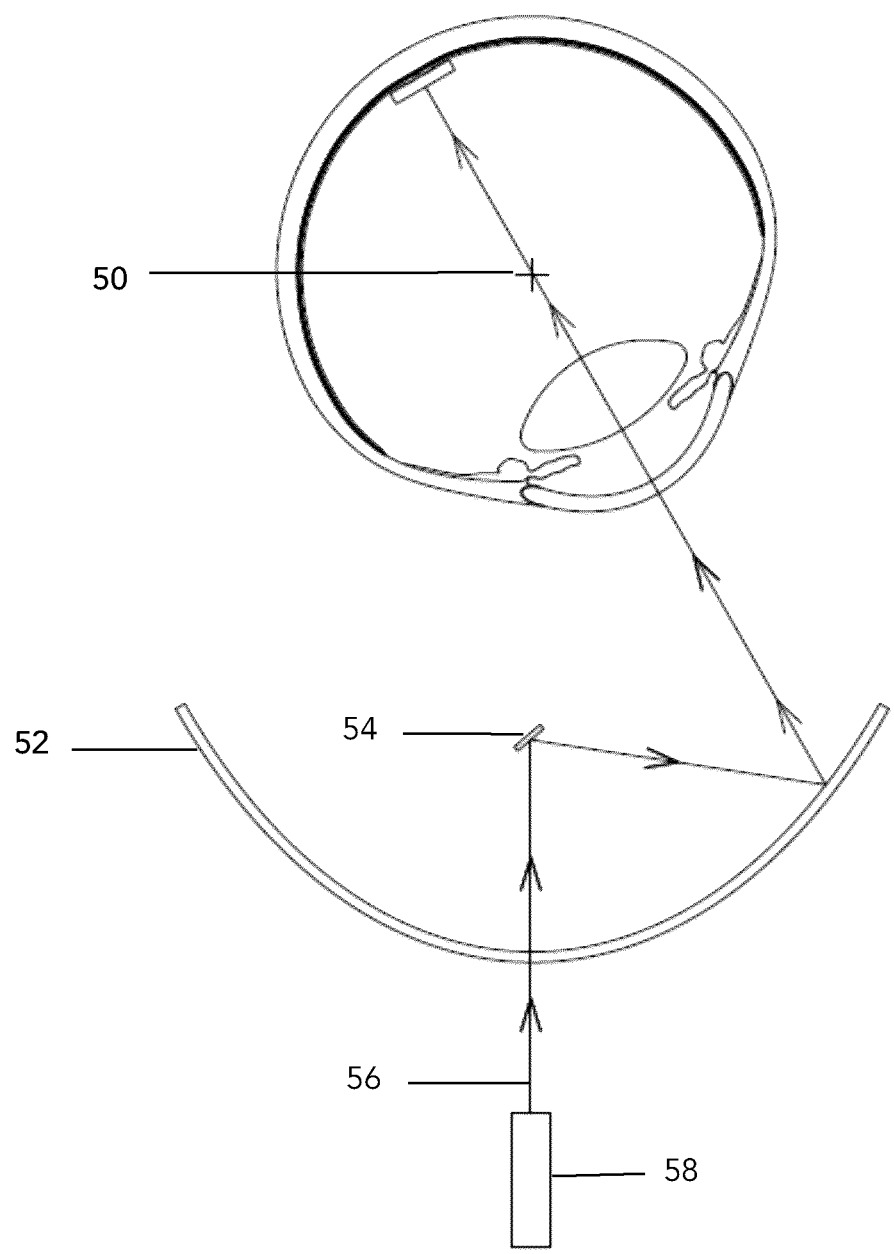
FIGS. 4A-4D illustrate examples of collimated beam steering.

For retinal implant applications wherein the source apparatus and the remote device may move with respect to each other within certain constraints, movements of the eye must be taken into account. One consideration is that the collimated beam does not traverse the sclera (the white part of the eye), thus, as the eye moves, the collimated beam must be deflected in such a way that it first enters the eye at normal incidence through the pupil and lands on the device. In the case where uninterrupted data and power transfer are desirable, continuous alignment of the modulated collimated beam onto the PV cell in the remote device should be enabled via an alignment feedback. In one configuration, the collimated beam and optical components are arranged such that the beam appears to originate directly from in front of the pupil. From there it enters the eye at a location centered on the pupil, going through the center of rotation of the eye and onto the PV cell on the device. In one example of this configuration, illustrated in FIG. 4A, a reflecting optical element 54 can be used to direct the collimated beam 56 from the collimated light source 58 onto a curved mirror 52, which is shaped in such a way as to reflect the collimated beam through the center of rotation of the eye and, from there, squarely onto the PV cell at the device. In one embodiment the curved mirror 52 has the shape of an elliptical mirror that is characterized with two focal points, with the primary focus placed at the reflecting optical element 54 and the secondary focus at the center of rotation of the eye 50. In another embodiment, the curved mirror can be made of glass or plastic/polycarbonate coated with a NIR-reflective substance, allowing visible light to enter the eye and be processed naturally by the person's remaining peripheral vision. The reflecting optical element 54 can also be a Micro-Electro-Mechanical Systems, or MEMS, mirror. The position of the reflecting optical element 54 is controlled by position tracking that compensates for any relative movement between the device and the collimated light source. Although not shown in FIG. 4A, the design applies to the horizontal and vertical axes.

Figure 4B:
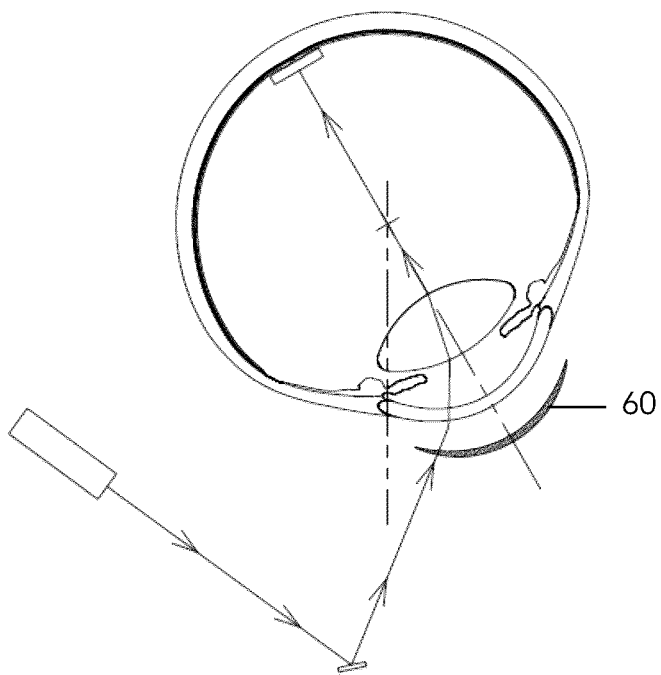
Figure 4C:
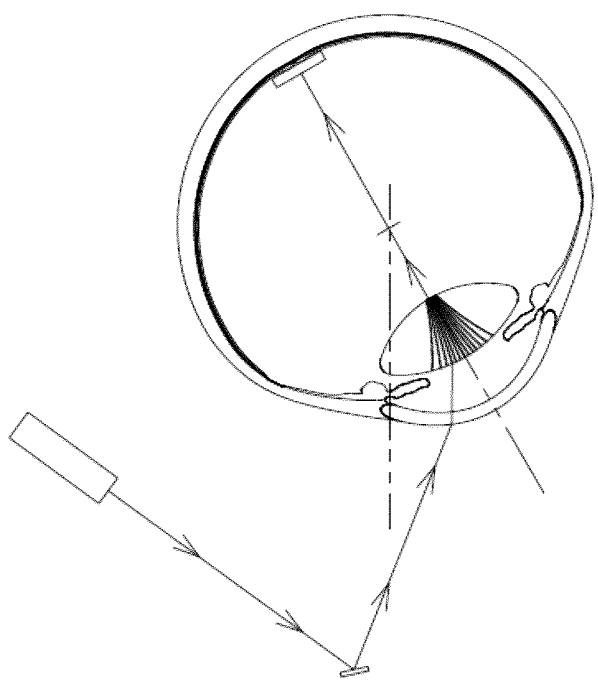

For a retinal implant application, the beam steering could also be implemented by modifying the optics of the eye. In FIG. 4B, the collimated beam is aimed at a steerable optical element, which directs the beam directly to the cornea. In this case, the collimated beam no longer appears to originate from in front of the pupil. A combination of specially designed optics, which could include the intraocular lens, cornea shaping (as in laser vision correction) and contact lens, curves the incoming beam to direct it at the device at the back of the eye. This scheme may be implemented with a series of convex and concave lenses. In another embodiment, the lens could be active, with the means to electronically control incoming rays. In another example, the eye optics could be replaced with a mesh of optical fibres that take the light entering the eye from any direction and channels it so that it focuses onto the PV cell of the device. FIG. 4C shows an intraocular lens that has been replaced with such a fibre optic arrangement.

Figure 4D:
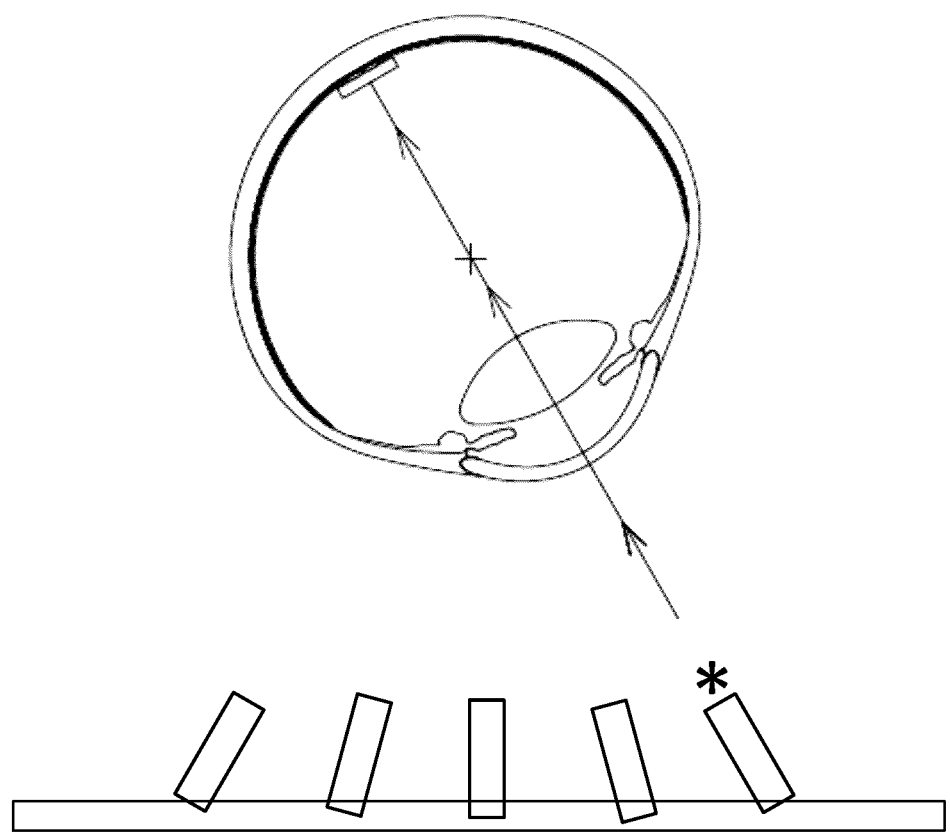

For a retinal implant application, the beam steering could also be implemented as an array of lasers pointing at the eye laid out on, for example, a pair of glasses. For this application, the average radius of the eye (to the centre of rotation) is 12.2 mm and eyeglasses can be about 50 mm from the device. Each laser is set at the proper angle to aim the laser beam at the device for a particular eye position, within the covered eye movement latitude. FIG. 4D illustrates one example of a tracking system that could switch the appropriate laser(s) to follow the eye movement and position.

For an application wherein the device and the source apparatus may move with respect to each other within certain constraints, a tracking system corrects any drift in position and limited motion. Several configurations of beam steering are possible. In one example, the collimated beam is positioned laterally and a steering optical component, controlled by the tracking system, keeps the collimated beam directed at the device.

Device Receiver

FIG. 5 is a block diagram of a receiver circuit for power harvesting and data recovery from the collimated beam at the device. The device extracts the power and the data from the electrical signal produced by the PV cell 100 in response to the incoming collimated beam. In one embodiment, the PV device is a PV cell which harvests the electrical signal from the collimated beam and feeds it to a splitter, where power and data are separated. In another embodiment, the PV device and the splitter are comprised of a PV cell and a photodiode, from a collimated beam carrying at least one wavelength. In another embodiment, the PV device and the splitter are comprised of a segmented PV cell with 2 segments: a large segment to harvest the power and a small segment to extract the data, from a collimated beam carrying at least one wavelength. In another embodiment the PV and photodiode are separate from one another.

For a system in which power and data is continuous, the reception of data at a sufficient rate will support the real-time transfer of information. Real-time transfer of information can be, for example, real-time video data received from a camera on the source apparatus. Such a data rate can be obtained, for example, in the forward link of the ASIC for the 256-electrodes array retinal implant (Tran et al., IEEE JOURNAL OF SOLID-STATE CIRCUITS, VOL. 49, NO. 3, MARCH 2014), which is 600 kbps. PV cells of small dimensions (surface of 3 $mm^2$ or less) with a response time sufficient to support this data rate can be found. In other cases a separate photodiode may be necessary. The combination of PV cell and photodiode thus enables receipt and conversion of modulated collimated light to electrical energy as well as data.

When the eyelid closes the collimated beam is interrupted. However, enough light may pass through the eyelid to keep the receiver operational in standby mode. The signal received by the receiver may be sufficient to continue to provide positional information to the source apparatus. The intensity of the collimated beam may be modified so as to maximize the efficiency of the PV cell.

Figure 5A:
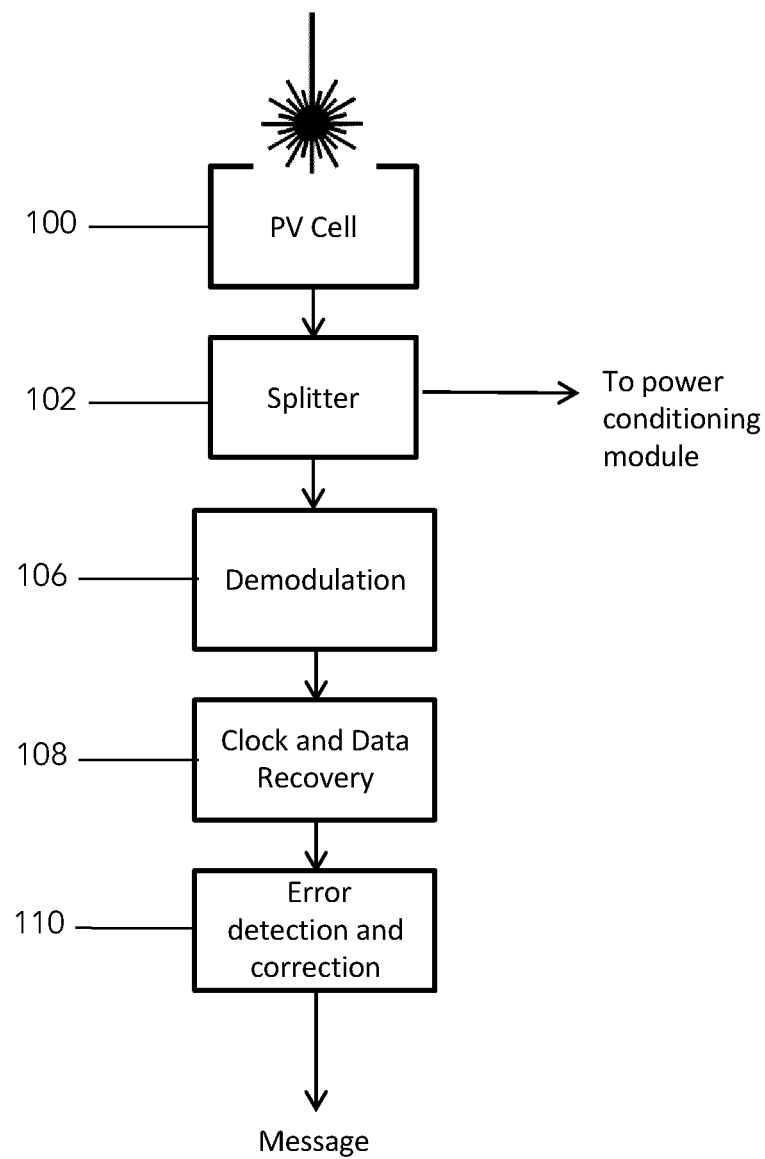
FIG. 5A is a block diagram of the receiver circuit of the device and power and data harvesting from the collimated beam sources.
Figure 5B:
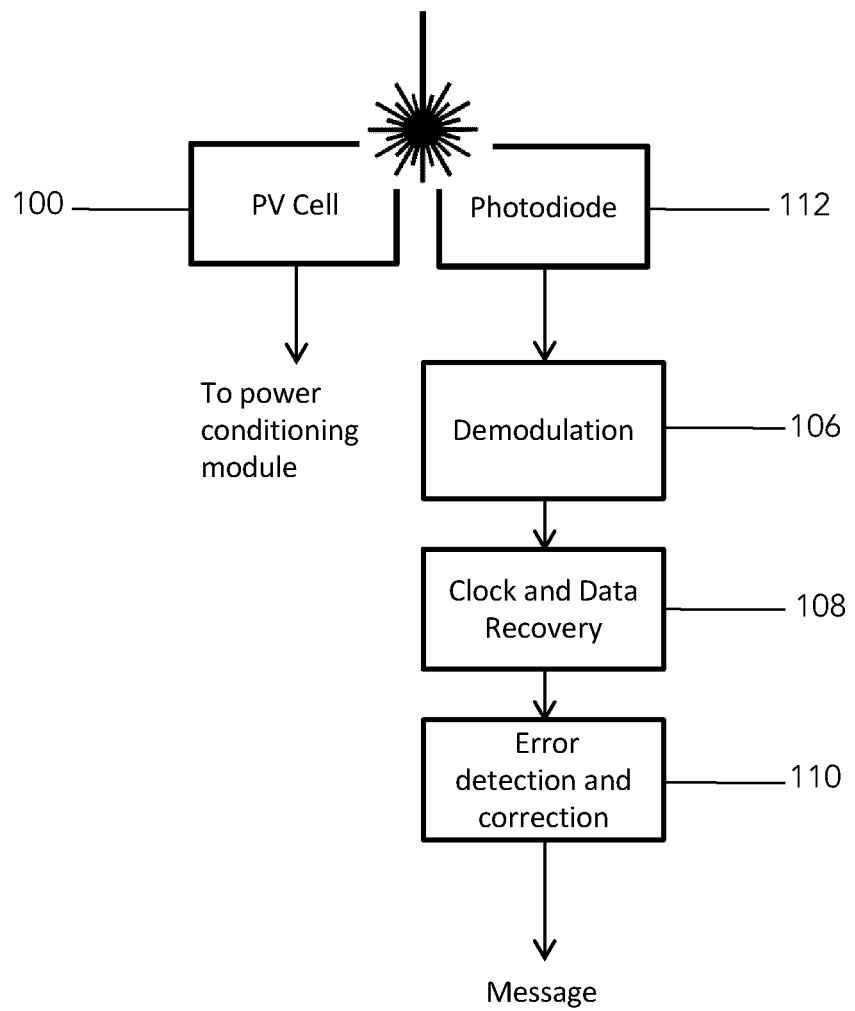
FIG. 5B is a block diagram of the receiver circuit where the PV cell harvests power and a separate photodiode harvests data.

FIGS. 5A and 5B show two embodiments of a receiver circuit on the remote device. In the embodiment illustrated in FIG. 5A, the receiver circuit comprises a PV cell 100 that converts the received modulated collimated beam into an electrical signal, and a splitter 102 that sends a portion of the electrical signal to a data recovery circuit and the bulk of the signal to a power conditioning module. The received signal is split into two at the splitter 102 (also shown in FIG. 3), one part containing the bulk of the electrical energy, and a much lower intensity signal which is directed to the data recovery circuitry. One preferred embodiment of the splitter is a resistive splitter. The demodulation module 106 recovers any signal that was modulated in the transmitter. If a modulation scheme was implemented, then a matched demodulation scheme is used. A clock and data recovery (CDR) module 108 extracts a clock from the self-clocking signal at its input and uses it to recover the bits encoded in the input signal. The output of the CDR module 108 consists of the recovered clock and the decoded bit stream. An error detection and correction module 110 detects and attempts to correct errors that may have been introduced in the bit stream by the imperfections of the channel such as reflections, refractions, multipath or noise; or by some misalignment of the collimated beam with the PV cell. The error detection and correction module 110 can include the calculation and verification of a cyclic redundancy check (CRC) or any other method used in the corresponding transmitter module. The output of this module yields the actual data.

FIG. 5B is a block diagram of the receiver circuit where the PV cell harvests power and a separate photodiode harvests data. In the embodiment shown in FIG. 5B, the receiver circuit has a receiver comprising a combination of a PV cell 100 a photodiode 112, working together such that the incoming collimated light signal is received by both PV cell and photodiode. The PV cell 100 and the photodiode 112 can be independent and wired together, or could also be on the same chip The processing unit processes the signal into useful information for the functions of the remote device. The processing unit may consist, for example, of a clock and data recovery circuit, a demodulator, a decoder, a processor or any other circuitry or a combination thereof. In one embodiment, the device houses a system on a chip (SoC) or a microcontroller which includes non-volatile memory, random-access memory (RAM) and a bootloader, enabling the downloading of new code into the processing unit. This enables the upgrading of software to new versions after the device has been put in service, to implement improved algorithms and methods as well as bug fixing without the need to service the device.

Multiple Devices

Figure 6:
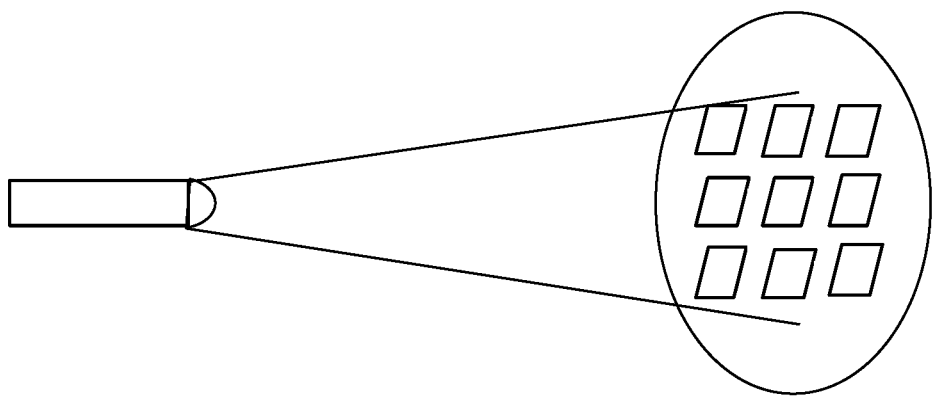
FIG. 6 is an illustration of a configuration comprising multiple devices.

FIG. 6 is an illustration of a configuration comprising multiple devices. In this configuration the transmitter on the external site transmits a signal to a plurality of co-located devices at a fixed distance from each other. The devices operate in a coordinated fashion in order to achieve a specific function. In one example, a tiling of devices placed in proximity of each other on substrate to function as a retinal implant, as each device stimulates a set of ganglion cells in its immediate geographical location. In one embodiment the substrate can be a flexible silicone bed. Effectively, a single larger device can be subdivided into an array of smaller devices arranged in a given configuration, each such device constituting an autonomous device. Such an arrangement allows the array of device to better conform to the shape of the organ, and the electrodes to be placed at an optimal distance from the tissue. For a retinal implant, this is an important factor for superior visual acuity and may enable improved vision to a degree not possible with a single large implant. Each individual device in the array receives power and data from a collimated beam via the steerable optical element, with the data sent and received being specific to each device. In one embodiment of the multiple devices or array configuration, the light sent to all devices simultaneously consists of a plurality of collimated beams at different wavelengths, each wavelength carrying the data for one specific device. A single reflecting optical element at the external site and a single collimated beam can then cover all the devices. The PV cell in each device can be tuned only to the frequency which it has been allocated, so that the data extracted from the received signal is data specific to the individual device. The wavelengths can be set apart according to the coarse wavelength division multiplexing (CWDM) scheme. In another example, a reflecting optical element can be associated to each beam of a given wavelength at the transmitter, so that each beam is directed at its target device. All the beams can then move together as a response to position tracking, however minute angle adjustments to each reflecting optical element can be made to account for the nonlinearity of the relative displacement from the perspective of the external collimated light source.

In another embodiment of the multiple devices or array configuration, a single collimated beam source, aligned with a single reflecting optical element and configured so that its size matches a single device, is directed at each device in sequence for a short duration, in a sweeping motion. Each device can then extract power and data from the signal while it is illuminated by the collimated beam. The beam intensity may be lowered while the collimated beam is in transition between two devices.

In another embodiment of the multiple devices configuration, a single collimated beam source, aligned with a single reflecting optical element, is configured such that its size covers all the devices, thus all devices receive the beam at all times. Each device can harvest the power on a continuous basis. The optical data signal contains the data for all the devices. Each device has an awareness of its identity and extracts the data that belongs to it from the bit stream. This can be done in a number of different ways. In one example, the data may contain a header identifying the target device, so that each device receives its data in sequence. In another embodiment, time multiplexing can be employed to address each tile separately.

Uplink Channel

An uplink channel relays information from the remote device to the source apparatus. The kind of information relayed by the device may include: the state and status of the device; telemetry information such as electrical parameters, device temperature, measurements at sensing electrodes; and feedback data related to beam alignment. The embodiments described below vary in their implementation complexity, the data rates supported, their geometrical and power requirements and their overall performance. In one embodiment of the uplink channel, the PV cell is designed such that a small area on its surface is positively biased so that it becomes a light emitter of a particular wavelength. This light emitter is modulated with the uplink data, and the light it produces is picked up by a photodiode matched to that wavelength on the source apparatus side. The light emitter produces a diffuse light, however the short distance between the light emitter and the external photodiode as well as the narrow bandwidth of the light produced aid in the detection of the signal. In another embodiment of the uplink channel, the reverse signal modulates a discrete laser diode. Laser diodes have been shown to transmit at data rates as high as 16 Mbps through a skin thickness of 4 mm with a bit-error rate (BER) of $1\times10^{-9}$ (Parmentier, S. et al. 2008 IEEE pp. 377-380).

Another embodiment of the uplink channel consists of a reflecting optical element that reflects a portion of the incoming collimated beam. In the path of the reflection, a material changes the intensity of the reflection in response to an electrical signal that carries the uplink data. At the source side, the modulated reflection is picked up by a photodiode which converts the fluctuation in light intensity to an electrical signal, from which the uplink data is extracted. In the preferred embodiment, the reflecting optical element is a retroreflector. A retroreflector consists of an arrangement of optical elements whose particularity is to reflect a beam directly back toward the source, a property which is desirable given the directionality of the incoming collimated beam and the possibility of displacement between the external apparatus and the device. In another embodiment, the reflecting optical element reflects or scatters the collimated beam in many directions, so that the reflection is no longer a directional beam and it can be detected from the source side anywhere in the coverage area, albeit at a lesser intensity. In yet another embodiment, the reflecting optical element is a MEMS mirror which oscillates in response to an electrical signal that carries the uplink data, causing a change in the intensity detected at the source photodiode.

On the remote device, an additional optical element may be implemented in a number of ways. Examples include a discrete component or the etching of a surface, such as the PV cell surface or the capsule material. One example of a material modulating the reflection is liquid crystal, which becomes opaque when an electric signal is applied to its electrodes. Another example of such a material is a piezoelectric actuator producing a displacement in the presence of an electric field, said displacement also changing the intensity of the reflection. Another example are quantum-well electro-absorption modulators. As mentioned in U.S. Pat. No. 4,143,263, other effects may also be taken advantage of, such as Kerr cells or Pockels cell.

In another embodiment of the uplink channel, a radio-frequency (RF) link carries the reverse data. A transmitter on the device may include a radio antenna which fits in the transparent capsule housing the electronics of the device. In another example, the antenna consists of a thin piece of metal incorporated within the diamond capsule after etching a very thin and relatively deep strip of the diamond capsule along its sides. With this method, little space is required inside the capsule to house the antenna. Such a transmitter at the device may include some of the functions described in the downlink transmitter on the external side, namely error detection and correction encoding, zero bias encoding and modulation. Bandwidth on RF links depends on the modulation scheme adopted and components performance. Data rates in the Mbps can be obtained with the appropriate digital signal processing scheme. The RF uplink can be active or passive and may use radio frequency identification protocol (RFID). The frequency of the uplink channel may include one or more of the ISM bands (Industrial Scientific and Radio Bands). Note that the RF uplink in this embodiment can operate even if the eyelid is closed.

Luminescence arising from the PV cell itself can also be used to encode the data in the uplink channel. In addition, the uplink channel can use RFID technology to encode the data. The uplink channel may also use differential magnetic coupling to encode the data.

Tracking

In the case of a retinal implant, the optical system of the eye can have a great effect on the incoming collimated beam. The eye optics converge incoming light onto the retina, particularly at the macula where the images appear in sharp focus. A collimated beam can be focused by a factor of 100,000 onto the retina (Laser Institute of America, Laser Safety Information). Thus, lasers can potentially cause damage to the eye in a very short time. Appropriate laser power levels and sufficient monitoring and tracking enable safe use of lasers to deliver power and data to remote devices in the eyes, and elsewhere in the body. The shape and size of the laser beam on the device can be configured for optimal operation of the system. For example, for a 3×3 mm device, a 'square top' shaped beam of 3 mm edge would best cover the PV cell, but it would start falling off the device in the presence of any displacement, reducing the illumination available for harvesting of power at the PV cell. A very narrow beam width does not take advantage of the whole surface and requires a higher intensity, which is undesirable for a bionic or implanted application. A configuration with a beam width somewhat smaller than the device size, for example between 1 mm and 2 mm for a 3 mm device, can tolerate some movement of the device while the beam remains on the PV cell. One example of a method to set the beam width is a mirror with the desired focal length.

In order to efficiently extract power from a collimated beam, the collimated beam must fall onto the PV cell. Therefore, alignment of the source of the collimated beam on the PV cell in the device is important to the present system, as a misaligned collimated beam may result in loss of the optical link between transmitter and receiver. It is further desirable that the remote device be continuously powered by the collimated beam to ensure smooth and predictable operation.

When the movement of the device and the source apparatus does not involve active motion between the collimated light source and the device, the tracking corrects for drift or relatively slow displacement. One example of such a system is a brain implant where the external apparatus is fixed onto the scalp in an unobtrusive location, such as behind the ear, and sends a collimated beam transdermally to a fixed-in-place implanted capsule with a PV cell.

Eye tracking has been the subject of a great deal of research over a long time, leading to the development of a number of methods to follow eye movement and position. The majority of those systems are based on pupil tracking or corneal reflection of an infrared or near infrared light. The corneal reflection, visible on the eye, is captured by a camera and the displacement of the reflection is calculated. Eye trackers generally only work when the eye is open. They are also designed to track the gaze, rather than the motion itself. Fast sampling rates of commercial eye trackers are in the range of 1-2 kHz. In the case of a retinal implant, where rapid motion is involved between the collimated light source and the device, high performance tracking is crucial to the system. Additionally, the device must receive power to operate during a blink and while the eye is moving. In one sample calculation, assuming a device of 3 mm$^2$ and a distance from the collimated light source of 5 cm and an angular speed of 700°/sec, the displacement corresponding to the beam moving 5% off the center of the device (0.15 mm) is about 1 ms. However, with a beam diameter of 1.5 mm, the beam would need to move by over 1.5 mm to start falling off the device. This would take approximately 10 ms. These numbers, 1 to 10 ms, provide an order of magnitude for the response time required of an eye tracking system for a maximal angular speed of 700°/sec. Therefore, some available eye tracking systems, with a response time of 1 to 2 kHz, would be fast enough for this application, although they also need to work during a blink and while the eye is in motion.

Figure 7:
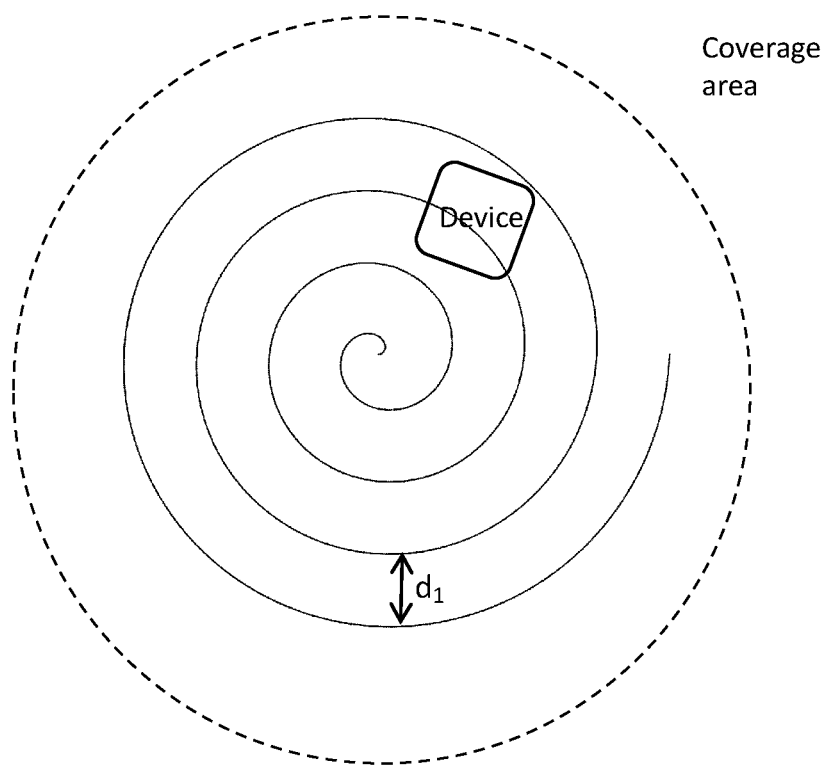
FIG. 7 shows an example of a search path from the estimated center of the field of view.

Continuous collimated beam delivery to the PV cell in the device can be achieved using a closed loop feedback system and an illumination detector for determining an illumination of the PV cell or the photodiode. Initial acquisition of the device location is required, followed by tracking of the device and steering correction. A major misalignment would require a re-acquisition of the device position. Initial acquisition of the device position is the determination of the device position in the entire area covered by the steering device. In one embodiment, the source apparatus aims the collimated beam in a search pattern, until a reflection or some other means is used to confirm detection of the device. There are several ways of doing a search pattern. In one example, illustrated in FIG. 7, the search pattern may use the initial location of the beam as a starting point and search in an outward spiral. Another example of a search pattern is a raster scan. Another example is to use deep learning or historical data on likely pupil positions as the initial starting points. The beam may progress through continuous movement or in steps. In another embodiment, the collimated beam illuminates the coverage area at a low intensity level while a camera aimed at the device on the source side takes a picture, which is processed to determine the device position. The position acquisition is completed with the reception of feedback from the device indicating that the collimated beam is properly directed at the device. In a preferred embodiment, on remote device tracking acquisition, a short high intensity collimated beam pulse is used to quickly charge the power supply capacitors on the remote device for fast start of the device.

Figure 8A:
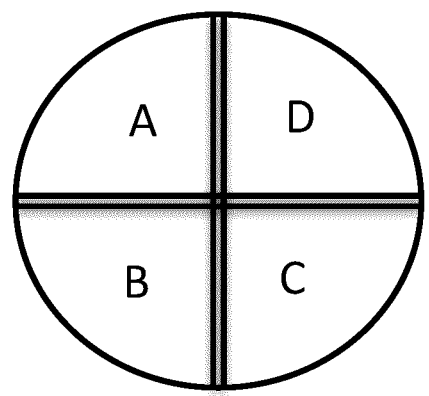
FIG. 8A depicts a quadrant detector comprising 4 photodiodes.
Figure 8B:
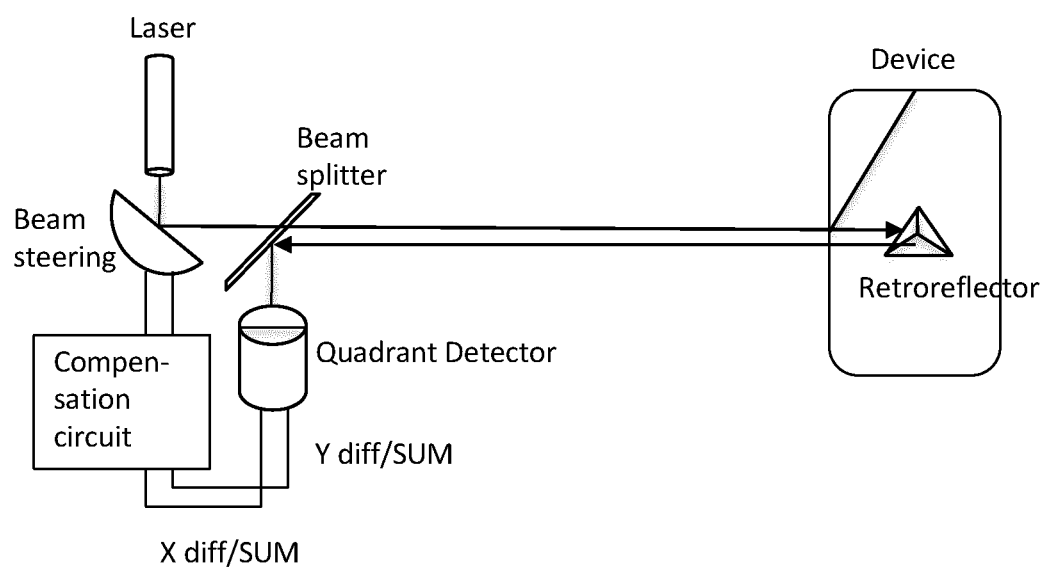
FIG. 8B illustrates an embodiment of the tracking system with the quadrant detector.

In one embodiment of the collimated beam tracking system, the illumination detector comprises a reflecting optical element which reflects a portion of the incoming collimated beam back to the source side, where it falls onto a quadrant detector. The preferred embodiment for a reflecting optical element is a retroreflector. A quadrant detector, illustrated in FIG. 8A, consists of four photodiodes that measure the amplitude of the reflected beam in each quadrant and output the displacement of that reflection in the X-axis and the Y-axis, as well as the SUM of the signal on all the photodiodes, so it is possible to get the weighed displacement values. These values are used by the compensation circuit to produce control signals for the beam steering to keep the collimated beam directed and aligned at the device. Another embodiment is shown in FIG. 8B and includes a beam splitter to direct the reflection onto the quadrant detector. Photodiodes are very responsive to changes in intensity. A typical rise time of quadrant detectors available on the market (for example the PDQ30C by Thorlabs) is better than 100 nsec, and bandwidth greater than 100 kHz. This performance surpasses the requirements for an eye implant application. This embodiment may be combined with the uplink channel embodiment where the intensity of the beam reflection on the device is modulated in response to an electric signal carrying the uplink data. The reflecting optical element at the device produces a reflection which is a directional beam. One preferred embodiment for the reflecting optical element is a retroreflector. In this system, on the source side, the single photodiode is replaced with a quadrant detector, and the uplink data is extracted from the SUM signal of the quadrant detector. A high pass filter removes the lower frequency displacement information from the SUM signal before it is sent to the uplink receiver for data extraction. The X and Y displacement signals are unaffected by the data modulation since they are normalized.

Figure 9A:
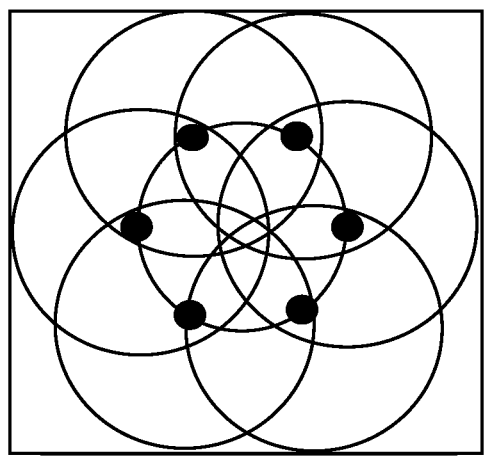
FIG. 9A shows a division of a single PV cell into 6 sections.
Figure 9B:
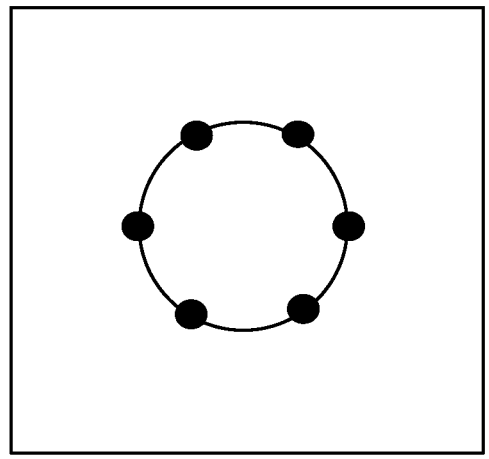
Figure 9C:
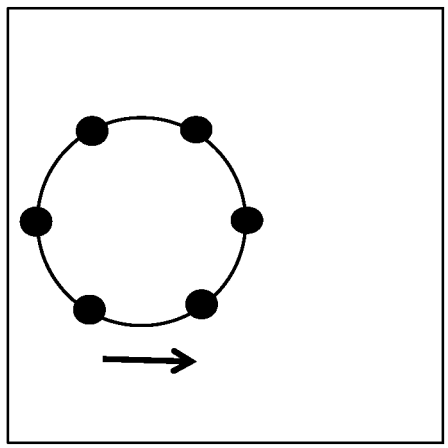
FIG. 9C shows an estimation to the left of the actual center of the PV cell.

In another embodiment of the tracking system, the illumination detector comprises a PV cell divided into a number of sections equidistant from the center, for example, in a pie shape. Measurements of the power generated by the PV cell are taken in each section to evaluate the intensity of the collimated beam, which will decrease if the beam is falling off the device in that section. When all sections have been measured, the information is sent to the source side through the uplink as position feedback and used to calculate a new estimate of the device position, and the cycle repeats. The beam width is optimized to maximize coverage of the PV cell while covering a section without too much of the beam area falling off the PV cell and providing differentiated readings. FIG. 9A illustrates one example device with a single PV cell having 6 sections and possible beam width optimization. FIG. 9B shows the case where the center of the PV cell is estimated properly (beam width removed). In FIG. 9C, the estimated center has moved to the left. Another example is a division of the PV cell into 4 sections, simulating a quadrant detector and making it easy to extract X and Y displacement of the beam. This method is well adapted to slow drift in time.

Figure 10A:
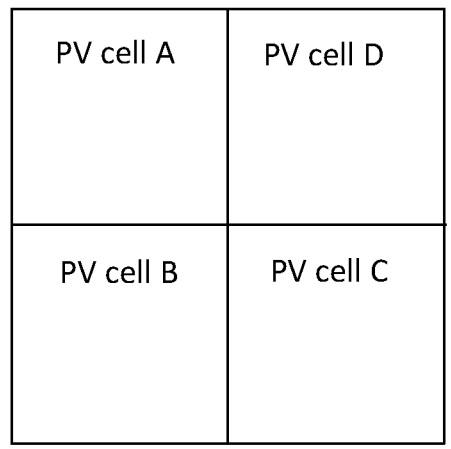
FIG. 10A depicts a device with four PV cells, one PV cell in each quadrant for a total of 4 PV cells.
Figure 10B:
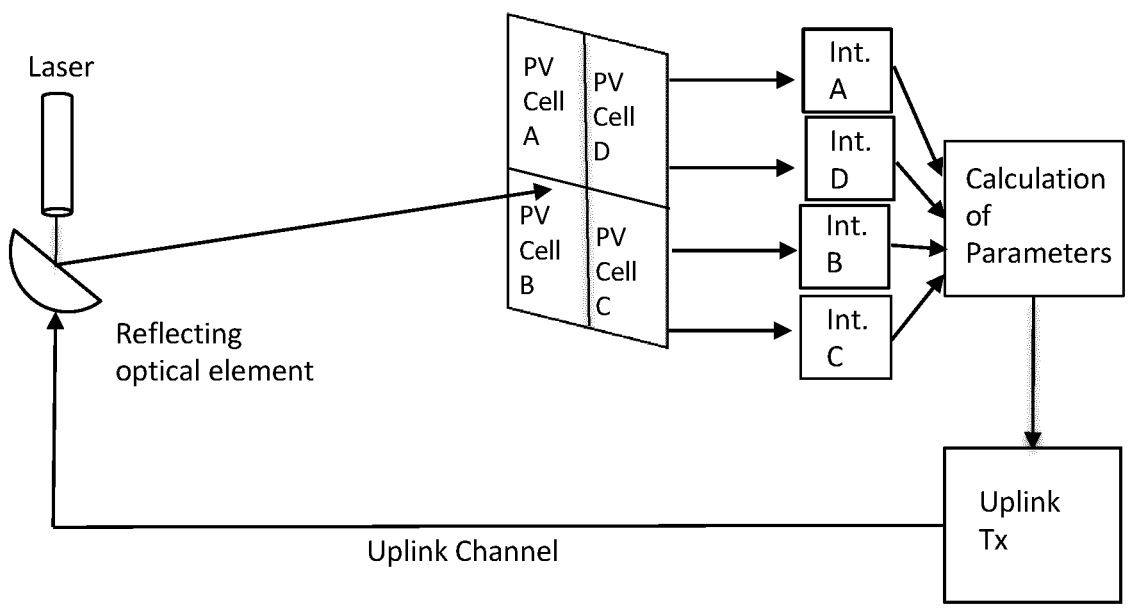
FIG. 10B shows an optical tracking system based on the same principle using 4 PV cells on the device.

In one variation of the tracking system, the device includes a grid of 4 PV cells which detect the beam intensity for the purpose of precisely aligning the collimated beam on the desired location on the device, as shown in FIG. 10A. One example of such a grid is a single PV chip with 4 separate photovoltaic cells. The collimated beam is aimed at the estimated centre of the device, and the illumination detector comprises 4 intensity values from a grid of PV cells which are measured and processed. The detection can be at the same time for precision and speed, or can be in sequence. One example of this system is illustrated in FIG. 10B. Processing takes place as previously described.

Figure 11:
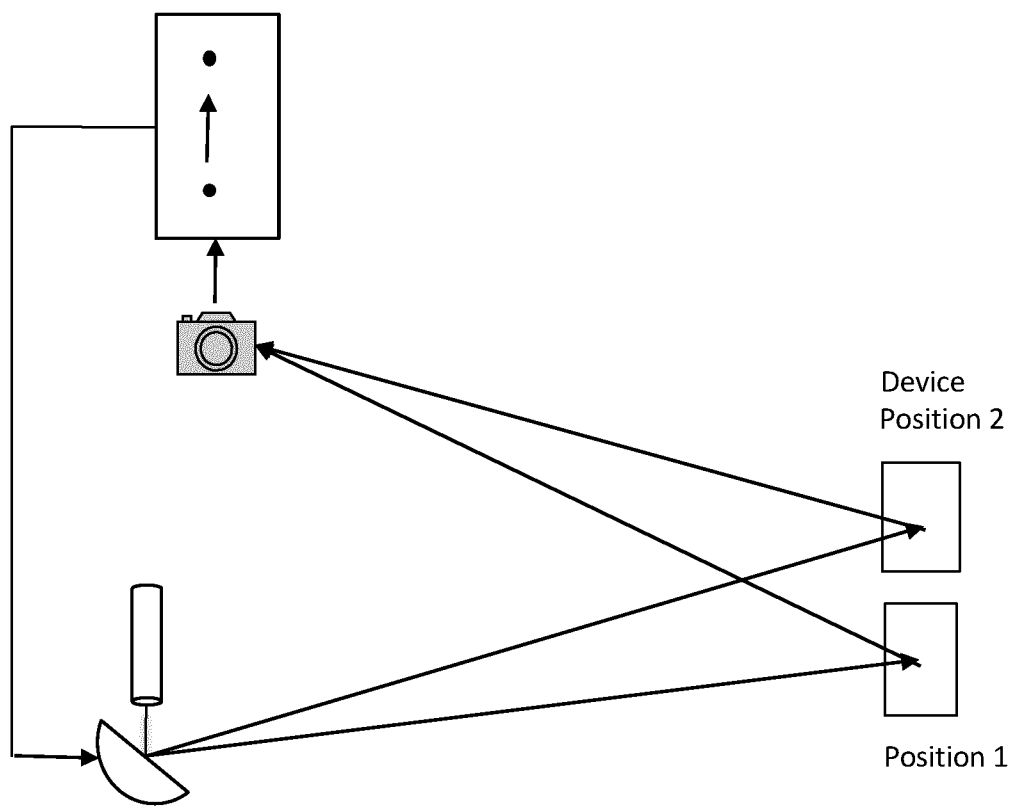
FIG. 11 depicts the moving reflection of the beam off the device as it is captured by a camera and processed to determine its displacement.

In another embodiment of the tracking system, illustrated in FIG. 11, the collimated beam is reflected off a reflecting optical element on the device, and is visible from a camera mounted on the source side and pointed toward the device. When the relative position of the device changes, the reflection moves as well. The current position of the reflection picked up by the camera is compared to its previous position in order to calculate displacement vectors used to correct the beam steering. For a retinal implant application, commercial eye tracking systems have optimized the tracking algorithms and could be used as is or serve as a basis in this embodiment. Another example is to use deep learning or historical data on likely pupil positions as the initial starting points. This embodiment could be used in combination with a point source of light on the device, for example a diode, either as a discrete component or incorporated in the PV cell, as described in the uplink embodiments above, and including the uplink system. The point source could improve the detectability of the device while providing a method for the uplink data.

Power Considerations

The power consumption of the remote device depends on its mode of operation while the harvested power depends on the characteristics of the optical system (transmission loss, reflectivity, etc.) specific to the system and on the parameters of the PV cell. Preferably, the harvested power corresponds to the power required by the device integrated circuit to minimize the occurrence of low-power events. Such a configuration can also prevent excess of power to the device which could be dissipated as heat. Such a situation could be detrimental to bioimplants and their surrounding environments. In order to best match the generated power to the load, the device can compute its average load value and send it to the source apparatus, which can then adjust the collimated beam power to match this value. The averaging time should be long enough to avoid responding to instantaneous load changes at the device. A loss of feedback signal from the device, as when the tracking of the device is lost, would cause the collimated light source to output a low power level that only needs to be strong enough to re-acquire the position of the device, thus avoiding the undesirable irradiation of surrounding tissues. Preferably, lasers used in this invention are categorized as class 1 or class 1M lasers, as defined in ANSI standard Z136.1.

The medium between the collimated light source and the PV cell must be sufficiently transparent with respect to the selected wavelength of the collimated beam to enable the beam to reach the PV cell through any layer and any protective capsule. With an optical system for a transdermal device, one must consider how tissue scatters and absorbs light that propagates through it. It is known that the skin is most transparent between wavelengths of 800 to 1300 nm. (See for example Ahnood et al. (Biosensors and Bioelectronics 77 (2016) 589-597). Furthermore, the PV cell must be highly efficient at harvesting the energy from the incoming collimated beam. In the case of a laser, this efficiency is highest when the energy of the incident photons (as determined by the laser wavelength) is close to the bandgap of the PV cell material, which is the energy required to excite an electron to the higher conduction band, so it can participate in conduction. For crystalline silicon (c-Si) and Gallium Arsenide (GaAs), common materials used for PV cells, this corresponds to wavelengths in the range of 885 to 1125 nm, which happens to overlap with the optimal wavelength range for skin transparency. It has been found that approximately 40% to 55% power conversion efficiency is achievable using crystalline silicon (c-Si) or gallium arsenide (GaAs) PV cells operated at near infrared wavelengths. Lastly, safety standards must allow sufficient intensity to be aimed at the body so that enough energy can reach the PV cell allowing it to harvest amounts of energy that can power a device. NIR benefits from a high safe tissue exposure limit (0.7-1.1 $W/cm^2$) depending on the beam type, duration and location (N. Stone and P. Matousek, Cancer Res. 68, 4424 (2008); S. K. Piper et al., PLoS ONE 8, e83749 (2013); International Commission on Non-Ionizing Radiation Protection, Health Phys. 105, 271 (2013); F. C. Delori et al., (J. Opt. Soc. Am. A Opt. Image Sci. Vis. 24, 1250 (2007)). The combination of long penetration depth, of high conversion efficiency of PV cells and of adequately high safe exposure power makes NIR ideal for energy delivery. Ahnood et al. (Biosensors and Bioelectronics 77 (2016) 589-597) have shown that when all these factors are taken into account, a PV cell illuminated with a matched 0.7 $W/cm^2$ laser at the optimal frequency of 980 nm will deliver a power output density of 20 $mW/mm^3$ transdermally, or a peak output power of 2.7 mW for a 1.5×1.5 mm PV cell. The authors mention that this output can be improved by optimizing several factors.

The combination optical power and data link can be used in the manufacture of retinal stimulators which have extensive surgical and geometrical constraints. The viability of optical power and data delivery is considered within limits of established safety standards on optical exposure of the eye. Based on F. C. Delori et al. (J. Opt. Soc. Am. A Opt. Image Sci. Vis. 24, 1250 (2007), table. 3), the maximum permissible power deliverable to the eye through natural pupil is 52 mW. Extended over a 3×3 mm PV area, this equates to 577 $mW/cm^2$ maximum power density. It has been previously calculated that this is approximately 10 times smaller than 5.6 $W/cm^2$ retinal damage threshold for over thousands of exposures and is consistent with the reported maximum safe power on the retina: 0.52 $W/cm^2$ at 905 nm, 0.88 $W/cm^2$ at 1000 nm and 0.28-0.8 $W/cm^2$ at 775-1000 nm. The power consumption of the retinal stimulator described by Tran et al. (IEEE Journal of Solid-State Circuits, Vol. 49, NO. 3, March 2014) is ~16 mW, comprising of base power (10 mW), and 64 electrodes operating at full intensities (64×90 µW). For a 256-electrodes device, the figures are 23 mW+10 mW=33 mW which is a maximal value if all electrodes are enabled at the same time. However, Tran et al. indicate that stimulation strategies do not typically turn on all electrodes together.

In the present technology, delivering about 16 mW electrical power to a chip requires a 3×3 mm PV cell with 50-55% efficiency to be receiving 29-32 mW of optical power. Based on a previously known transmission value of 70-82% through an uncoated/unprocessed diamond capsule, 36-46 mW of optical power is recommended for a diamond encapsulated device. This is within the 52 mW maximum permissible radiant power limit. The maximum optical transmission through the eye is known to be about 83%. Over the stated PV cell dimensions of 3×3 mm, this has been previously shown to correspond to 394-508 mW/cm$^2$, which is well within safe exposure limit. Inherent variabilities in the optical properties of different tissues, such as patient and body organ variabilities, and the performance of different PV technologies will lead to a range of optimum designs for various medical prostheses.

The source apparatus can further have connectivity to the internet and provide that connectivity to the remote device(s). Further, the power source may be on a wearable device such as a pair of eyeglasses, earring, earphone, or other wearable.

All publications, patents and patent applications mentioned in this specification are indicative of the level of skill of those skilled in the art to which this invention pertains and are herein incorporated by reference. The invention being thus described, it will be obvious that the same may be varied in many ways. Such variations are not to be regarded as a departure from the scope of the invention, and all such modifications as would be obvious to one skilled in the art are intended to be included within the scope of the following claims.

The embodiments of the present invention for which an exclusive property or privilege is claimed are defined as follows:

1. A system for wirelessly providing power and data to a remote device, the system comprising:
    a source apparatus comprising:
        a light source for generating a modulated collimated beam;
        a steerable optical element; and
        a wireless uplink receiver; and
    a remote device comprising:
        a receiver for receiving modulated light from the modulated collimated beam and converting the modulated light into an electrical power component and a signal component, the receiver comprising a photovoltaic cell and a splitter for splitting the output from the photovoltaic cell into an electrical power component and a signal component;
        a processing unit for processing a signal component of the modulated light;
        a power conditioning unit for conditioning electrical energy from the power component for powering the device;
        an illumination detector for determining an illumination of the optical signal reaching the receiver and aligning the collimated beam; and
        an uplink channel in communication with the wireless uplink receiver to relay feedback data related to collimated beam alignment to position the steerable optical element.

2. The system of claim 1, wherein the photovoltaic cell is for receiving the electrical power component and the receiver further comprises a photodiode for receiving the signal component.

3. The system of claim 1, wherein the uplink channel consists of radiofrequency, light emitting diode, or optical reflection modulation transmission.

4. The system of claim 1, wherein the reflecting optical element comprises a Micro-Electro-Mechanical Systems (MEMS) mirror, e curved mirror, or lens.

5. The system of claim 1, wherein the source of the collimated beam is a laser, near infrared laser, or light emitting diode.

6. The system of claim 1, wherein the remote device is a bioimplant.

7. The system of claim 1, wherein the remote device comprises an electrode array.

8. The system of claim 1, wherein the remote device is a retinal implant, visual cortex stimulator, spinal cord stimulator, cochlear implant, neuronal recorder, mid-brain implant, neuronal stimulator, cardiac pacemaker, cardioverter defibrillator, recording device, neuromuscular stimulator, or drug pump.

9. A wireless device for receiving power and data from a modulated collimated beam, the device comprising:
    a receiver for receiving modulated light from the modulated collimated beam and converting the modulated light into an electrical power component and a signal component, the receiver comprising a photovoltaic cell for converting an optical signal from the modulated collimated beam into an electrical signal and a splitter for splitting the electrical signal from the photovoltaic cell into a power component and a signal component;
    a processing unit for processing the received signal;
    a power conditioning unit for processing electrical energy from the power component for powering the device;
    an illumination detector for determining an intensity of the optical signal reaching the photovoltaic cell; and
    an uplink channel to relay feedback data related to collimated beam alignment for positioning the modulated collimated beam on the receiver.

10. The device of claim 9, wherein the photovoltaic cell is for receiving the electrical power component and the receiver further comprises a photodiode for receiving the signal component.

11. The device of claim 9, wherein the source of the collimated beam is a laser beam or a light emitting diode.

12. The device of claim 9, further comprising at least two electrodes for delivering at least one electrical pulse to tissue based on received data, for sensing an electric field around the electrodes, or both.

13. The device of claim 9, wherein the remote device comprises an electrode array.

14. The device of claim 9, wherein the remote device is a retinal implant, visual cortex stimulator, spinal cord stimulator, cochlear implant, neuronal recorder, mid-brain implant, neuronal stimulator, cardiac pacemaker, cardioverter defibrillator, recording device, neuromuscular stimulator, or drug pump.

15. A method for fine tracking a location of a wireless device by a collimated beam, the method comprising:
    directing the collimated beam onto a receiver divided in a plurality of segments;
    measuring an illumination received by each of the plurality of segments;
    reverse linking each of the plurality of segments to feedback values related to measured beam intensity; and
    aligning the collimated beam onto the receiver based on the feedback values using a steerable optical element, wherein the illumination of each of the plurality of segments is computed by a processing unit and sent through the reverse link to align the position of the beam on the plurality of segments.

16. The method of claim 15, wherein the receiver comprises at least one PV photovoltaic cell.

17. The method of claim 15, wherein the source of the collimated beam is a laser or a light emitting diode.

* * * * *